United States Patent [19]

Buendia et al.

[11] Patent Number: 5,399,685

[45] Date of Patent: Mar. 21, 1995

[54] PROCESS FOR THE PREPARATION OF 20-KETO-21 ALPHA-0l-STEROIDS

[75] Inventors: Jean Buendia, Le Perreux Sur Marne; Véronique Crocq, Paris; Christian Masson, Mouy; Denis Prat, Pantin; Michel Vivat, Lagny Sur Marne, all of France

[73] Assignee: Roussel-Uclaf, France

[21] Appl. No.: 75,822

[22] Filed: Jun. 11, 1993

[30] Foreign Application Priority Data

Jun. 11, 1992 [FR] France ................... 92 07047

[51] Int. Cl.$^6$ .................... C07J 9/00; C07J 75/00; C07J 33/00; C07J 21/00
[52] U.S. Cl. .................................. 540/30; 540/34; 552/524; 552/540; 552/544; 552/546; 552/548; 552/552; 552/553; 552/556; 435/51; 435/52; 435/53; 435/55; 435/61
[58] Field of Search ............... 552/546, 552, 556, 544, 552/524, 540, 553, 548; 540/30, 34; 435/51, 52, 53, 55, 61

[56] References Cited

U.S. PATENT DOCUMENTS 4,181,720  1/1980  Marx et al. ................... 424/241
4,273,771  6/1981  Coussediere ................. 424/242

FOREIGN PATENT DOCUMENTS 574317  12/1993  European Pat. Off. .

Primary Examiner—Johann Richter
Assistant Examiner—Kimberly J. Kestler
Attorney, Agent, or Firm—Bierman and Muserlian

[57] ABSTRACT

A process for the preparation of a compound of the formula

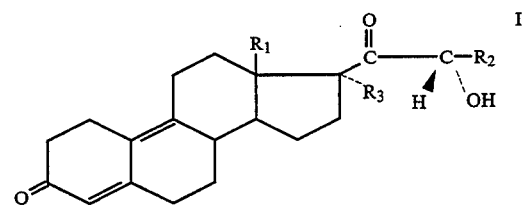

wherein $R_1$ is alkyl of 1 to 3 carbon atoms, $R_2$ is alkyl of 1 to 12 carbon atoms, $R_3$ is alkyl of 1 to 4 carbon atoms comprising reacting a compound of the formula

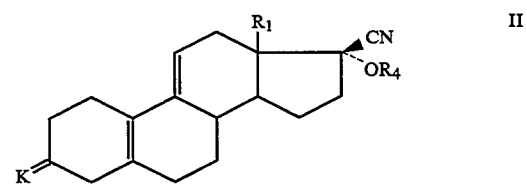

wherein $R_4$ is a remainder of an easily cleavable ether, K is a protected ketone function in the form of ketal, thioketal or mixed ketal and $R_1$ has the above definition with a magnesium organic compound reagent of the formula

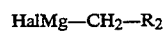

$$HalMg-CH_2-R_2 \qquad A$$

wherein Hal is a halogen and $R_2$ is defined as above to obtain a compound of the formula

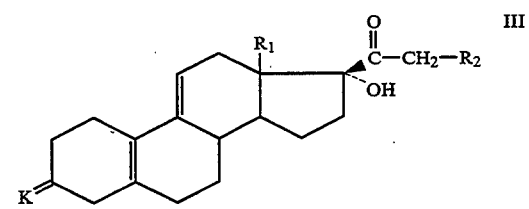

wherein $R_1$, $R_2$ and K are defined as above, reacting the (Abstract continued on next page.)

Abstract—continued latter with an acylation agent to obtain a compound of the formula

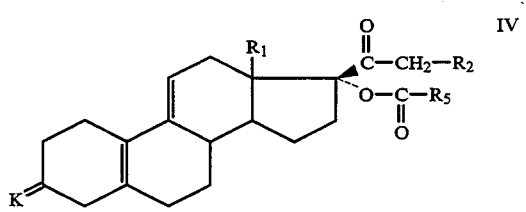

wherein $R_5$ is alkyl of 1 to 6 carbon atoms or aryl of 6 to 10 carbon atoms and $R_1$, $R_2$ and K are defined as above, reacting the latter with an appropriate alkylation agent to obtain a compound of the formula

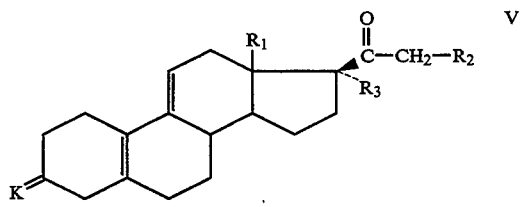

wherein $R_1$, $R_2$, $R_3$ and K are defined as above, subjecting the latter to autoxidation to obtain a compound of the formula

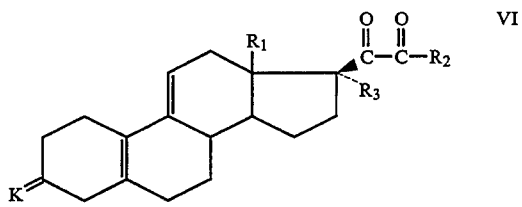

wherein $R_1$, $R_2$, $R_3$ and K are defined as above, reacting the latter with an acid to obtain a reconjugated 3-keto compound of the formula

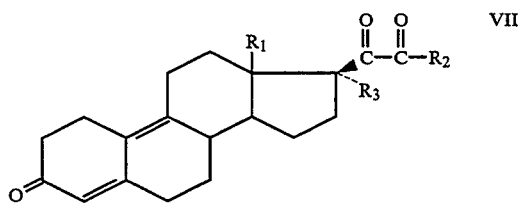

wherein $R_1$, $R_2$ and $R_3$ are defined as above and reacting the latter with a regio- and enantioselective reducing agent to obtain a compound of formula I and intermediates formed therein.

13 Claims, No Drawings

PROCESS FOR THE PREPARATION OF 20-KETO-21 ALPHA-01-STEROIDS

OBJECTS OF THE INVENTION

It is an object of the invention to provide an improved process for the preparation of 20-keto-21α-ol-steroids and novel intermediates therefore.

This and other objects and advantages of the invention will become obvious from the following detailed description.

THE INVENTION

The novel process of the invention for the preparation of a compound of the formula

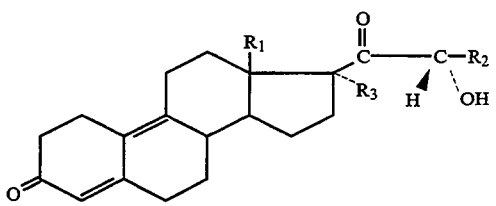

wherein $R_1$ is alkyl of 1 to 3 carbon atoms, $R_2$ is alkyl of 1 to 12 carbon atoms, $R_3$ is alkyl of 1 to 4 carbon atoms comprises reacting a compound of the formula

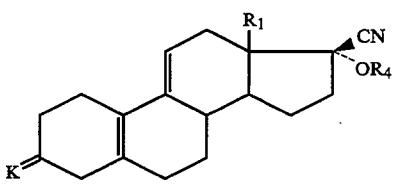

wherein $R_4$ is a remainder of an easily cleavable ether, K is a protected ketone function in the form of a ketal, thioketal or mixed ketal and $R_1$ has the above definition with a magnesium organic compound reagent of the formula

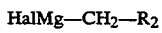   A wherein Hal is a halogen and $R_2$ is defined as above to obtain a compound of the formula

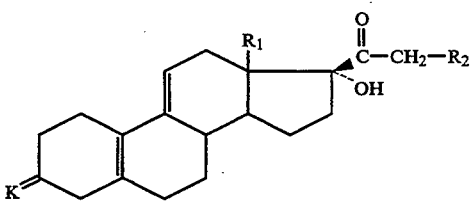

wherein $R_1$, $R_2$ and K are defined as above, reacting the latter with an acylation agent to obtain a compound of the formula

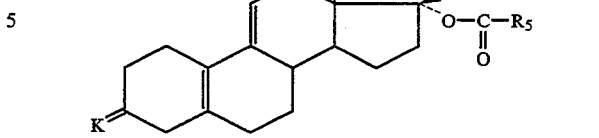

wherein $R_5$ is alkyl of 1 to 6 carbon atoms or aryl of 6 to 10 carbon atoms and $R_1$, $R_2$ and K are defined as above, reacting the latter with an appropriate alkylation agent to obtain a compound of the formula

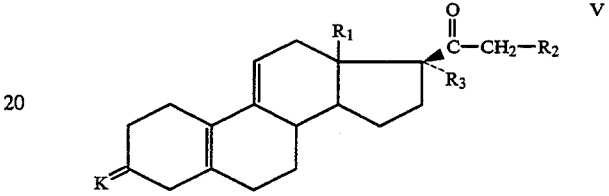

wherein $R_1$, $R_2$, $R_3$ and K are defined as above, reacting the latter with an autoxidation agent to obtain a compound of the formula

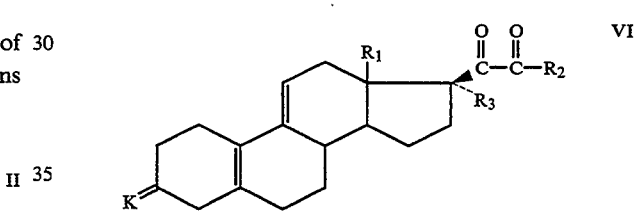

wherein $R_1$, $R_2$, $R_3$ and K are defined as above, reacting the latter with an acid to obtain a reconjugated 3-keto compound of the formula

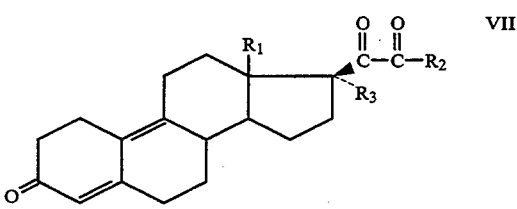

wherein $R_1$, $R_2$ and $R_3$ are defined as above and reacting the latter with a regio- and enantioselective reducing agent to obtain a compound of formula I.

Examples of $R_1$ are methyl, ethyl or propyl, with methyl being preferred and examples of $R_2$ are methyl, ethyl, propyl, isopropyl, n-butyl, isobutyl, n-pentyl, n-hexyl, 2-methylpentyl, 2,3-dimethylbutyl, n-octyl and 2,2-dimethyl-hexyl. Examples of $R_3$ are methyl, ethyl or n-propyl.

Examples of K are

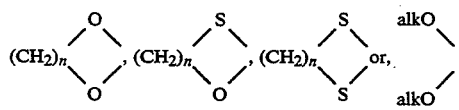

n being 2 or 3 and alk is alkyl of 1 to 4 carbon atoms.

Examples of $R_4$ are alkyl of 1 to 6 carbon atoms such as methyl, ethyl or propyl, tetrahydropyranyl, aryl of 6 to 12 carbon atoms such as phenyl optionally substituted by one or more methyls, a silylated group, such as trialkylsilyl such as trimethyl or dimethyl terbutylsilyl, triarylsilyl such as triphenylsilyl, or diarylalkylsilyl such as diphenylter-butylsilyl. Trialkylsilyl, particularly trimethylsilyl, is particularly preferred.

The reaction of the compound of formula II with the magnesium-compound reagent of formula A is carried out preferably in an ether, such as ethyl ether, tetrahydrofuran, dioxane, or in an aromatic solvent such as benzene or toluene, or also in a mixture of these solvents. In formula A, Hal is bromine, chlorine or iodine. The hydrolysis leading to the $17\alpha$-OH compound can be carried out with ammonium chloride, with a monoalkali metal phosphate or also with a weak acid such as acetic acid.

The acylation agent reacted with the compound, of formula III is preferably an appropriate acyl anhydride or halide. $R_5$ can particularly be methyl, ethyl, propyl or butyl, or phenyl optionally substituted by one or more methyls. The acylation agent is preferably acetic anhydride or acetyl chloride. The operation takes place in the presence of a base which can be, a nitrogenous base such as pyridine, 4-dimethylamino-pyridine or also triethylamine, in an inert solvent such as benzene, toluene, xylene or cyclohexane or in the absence of solvent.

The alkylation agent can be an alkyl halide or sulfate, the iodide being particularly preferred. The reaction is carried out in the presence of a strong basic agent which can be an alkali metal amide or alcoholate at low temperature in an appropriate anhydrous solvent, particularly an ether such as tetrahydrofuran.

The autoxidation reaction consists of reacting molecular oxygen on a compound which has been subjected to the action of a strong base beforehand which converts the 20-keto function into the corresponding enolate. The strong base can be an alkali metal alcoholate such as sodium or potassium methylate, ethylate or terbutylate or sodium teramylate, an alkali metal hydride or an alkali metal amide, example lithium, sodium or potassium. The oxygen is preferably introduced by bubbling it through the medium or by bubbling air through. The operation takes place in an organic solvent which can be for example dimethylformamide, dimethylsulfoxide or dimethoxyethane.

The unblocking of the ketone in positions can, according to the value of K, be carried out in different ways. An acidic agent in an aqueous medium is used in the case where K is a ketal. It can be for example a mineral or organic acid such as the following acids: hydrochloric acid, hydrobromic acid, sulfuric acid, perchloric acid, nitric acid, p-toluene sulfonic acid, acetic acid, formic acid, oxalic acid or a mixture of acids, or also an acidic resin, such as a sulfonic resin. In the case where K is thioketal or a mixed ketal, the deprotection of the 3-oxo function is carried out by the action of iodine in the presence of a base, such as, an alkali metal bicarbonate, or by the action of iodine in catalytic quantity in the presence of an oxidizing agent, notably hydrogen peroxide, by the action of methyl iodide, glyoxylic acid, or also metal salts such as mercury or cadmium. In general, the operation can take place in a solvent such as a lower alkanol, such as methanol or ethanol, in a mixture with a halogenated solvent, for example methylene chloride, in the presence of water.

For unblocking a thioketal or a mixed ketal, a product of deconjugated 3-keto type is obtained intermediately of the formula

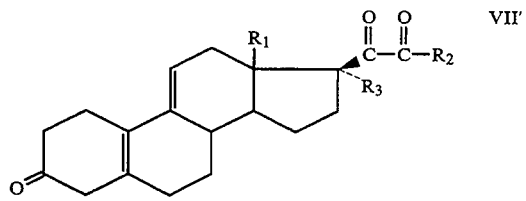

from which thee derivative of formula VII obtained by acid treatment under the conditions indicated above.

The regio- and enantioselective reduction of the compound of formula VII can be carried out by an enzymatic route. In the preferred conditions for implementing this process, the reduction is achieved by the action of a yeast, particularly a yeast chosen from the class of Hemiascomycetidae and preferably from the Saccharomycetacea family of which the Saccharomyces, Kluyveromyces and Schizosaccharomyces or Octosporomyces genera are part. The *Saccharomyces cerevisiae* yeast is quite particularly preferred.

The reaction can take place in a solvent or a mixture of solvents, such as hexane, toluene, alkanols with 1 to 12 carbons such as ethanol, isopropanol or dodecanol, dimethylformamide, dimethylsulfoxide, tetrahydrofuran. The operation takes place in the presence of a carbonaceous substrate which can be glucose, glycerol or ethanol and can take place in the presence of a sequestering agent of cyclodextrin type. The operation takes place at a pH which is preferably between 3 and 7 and at a temperature which can be between 25° and 50°C.

In a variation of the process of the invention, the compound of formula II is used wherein $R_4$ is trialkylsilyl and particularly trimethylsilyl and K is a ketal group and particularly ethylene ketal and the acylation agent reacted with the compound of formula III is acetic anhydride or acetyl chloride or bromide. The alkylation agent is an alkyl halide or sulfate and the operation takes place in the presence of an alkali metal amide or alcoholate and the autoxidation reaction is carried out by bubbling through of oxygen or air on an enolate in position 20 obtained by the action of a strong base, particularly an alkali metal alcoholate or amide, on the compound of formula V.

The acid treatment of the compound of formula VI in which K is a ketal group is carried out with a mixture of acetic acid—perchloric acid or aqueous hydrochloric acid and the reduction is carried out with a yeast chosen from the group above and particularly Saccharomyces cerevisiae.

In a preferred mode of the invention, the compound of formula II has $R_1$ as methyl and in the reagent of the formula A, $R_2$ is methyl and the alkylation agent is a methylation agent.

In an obvious variant of the process, the compound of formula II has the formula

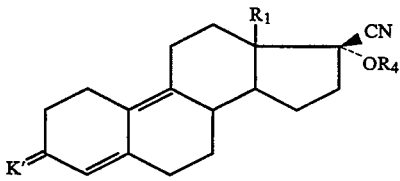

wherein $R_1$ and $R_4$ are defined as above and K' is a protected ketone function in the form of a thioketal. The other corresponding intermediates are obtained comprising a system of double bonds identical to those above and then after deblocking, the compound of formula VII and then the compound of formula I are obtained.

The new industrial compounds are the compounds of the formula

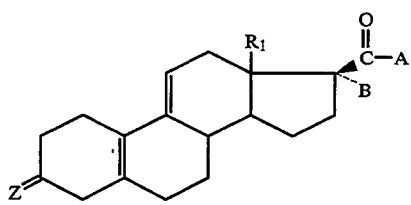

in which $R_1$ is defined as above and either Z is K, K as defined above and either A is —$CH_2$—$R_2$ and B is —OH or —O—CO—$R_5$, $R_2$ and $R_5$ being defined as above, or A is —CO—$R_2$ and B is $R_3$, $R_2$ and $R_3$ being defined as above, or Z is oxygen, A is —CO—$R_2$ and B is $R_3$, $R_2$ and $R_3$ being defined as above, or Z is K, A is —$CH_2$—$R_2$ and B is $R_3$, K, $R_2$ and $R_3$ being defined as above, with the exception of the compound wherein Z is ethylenedioxy, $R_1$ and B are methyl and A is —$CH_2$—$CH_3$; and the compounds of formula VII as defined previously.

Apart from their use as intermediates within the scope of the process, the compounds of formula V can also lead to certain compounds of the type of those described in French Patent No. 2,149.302 or to similar compounds, and in particular 17α-methyl 17α-(1-oxopropyl)-4,9,-estradien-3-one, by unblocking the ketone function in position 3 by the methods described above.

The compounds of formula I have progestomimetic and anti-oestrogen activities and are described in European Patent No. 7823.

The starting compounds of formula II are described in French Patent No. 2,082,129, or can be prepared by processes known to a man skilled in the art from the compounds described in this Patent or known otherwise. The compounds of formula II' can be obtained by processes known to a man skilled in the art, from the corresponding 3-keto compounds.

In the following examples, there are described several preferred embodiments to illustrates the invention. However, it is to be understood that the invention is not intended to be limited to the specific embodiments.

EXAMPLE

17α-methyl 17β-(2S-hydroxy 1-oxopropyl)-4,9-estradien-3-one

STEP A: cyclic 3-(1,2-ethanediyl) acetal of 17β-1-(oxopropyl)-5(10), 9(11)-estradien-17α-ol-3-one 30 ml of anhydrous tetrahydrofuran and 20 ml of a 3M solution of ethyl-magnesium bromide in ethyl ether were mixed together under an inert gas atmosphere and 3.63 g of cyclic 3-(1,2-ethanediyl) acetal of 17α-trimethylsilyloxy-17β-cyano-5(10), 9(11)-estradien-3-one in solution in 10 ml of tetrahydrofuran were added slowly at ambient temperature. The reaction medium was gently heated to eliminate the ethyl ether and to reach a concentration of about 2M of the magnesium-compound. Then, the reaction medium was held at +64°/+65° C. for 16 hours and then cooled to +15°/+20°C. 25 ml of a saturated solution of ammonium chloride were poured into it while controlling the temperature with a water and ice bath, and then another 40 ml of a saturated solution of ammonium chloride were poured in. The mixture was stirred for 1 hour at 25° C. and the attraction took place with methylene chloride. The organic phase was washed with water, dried and the solvent was evaporated. The residue was chromatographed on silica eluting with a toluene-ethyl acetate mixture (85–15) to obtain 2.7 g of the expected product melting after crystallization from isopropyl ether at 159° C.

IR Spectrum (CHCl$_3$) Absorptions at 3618 and 3513 cm$^{-1}$ (OH), 1706 and 1691 cm$^{-1}$ (C=O), 1640 and 1617 cm$^{-1}$ (C=C). NMR spectrum (CDCl$_3$ 300 MHz, ppm) 0.23 (s), 0.66 (s): 18-CH$_3$; 1.07 (t): CH$_3$ of the propyl; 2.45–2.80: —CH$_2$— of the propyl; 3.99: ketal; 5.57: H$_{11}$.

STEP B: cyclic 3-(1,2-ethanediyl) acetal of 17α-acetoxy-17β-(1-oxopropyl)-5(10), 9(11)-estra-dien-3-one 1.7 g of the product of Step A, 17 ml of toluene and 0.34 g of 4-dimethylamino-pyridine were mixed together under an inert gas atmosphere and 0.9 ml of acetic anhydride were introduced slowly with stirring. The mixture was refluxed for approximately 40 hours and then cooled to 0°/+5° C. 10 ml of ethyl acetate, then 34 ml of a saturated aqueous solution of ammonium chloride were added and the mixture was stirred for 1 hour at 0°/+5° C., followed by decanting and extracting the aqueous phase with ethyl acetate. The combined organic phases were washed with water, dried and the solvent was evaporated. The residue was taken up in isopropyl ether, the crystals were separated and dried to obtain 1.98 g of the expected product melting at 195° C.

IR Spectrum (CHCl$_3$) Absorptions at 1729–1715 cm$^{-1}$ (C=O), presence of ketal, absence of OH. NMR spectrum (CDCl$_3$, 300 MHz, ppm) 0.53 (s): 18 CH$_3$; 1.05 (t): CH$_3$ of the propyl; 2.07 (s): O—AC; 3.99 (ketal); 5.58: Hhd 11.

STEP C: cyclic 3-(1,2-ethanediyl) acetal of 17α-acetoxy-17β-(1-oxopropyl) -5(10), 9(11)-estra-dien-3-one 8 ml of liquid ammonia and 33 mg of lithium were mixed together under an inert gas atmosphere at −70° C. and after stirring for 15 minutes, 10 ml of anhydrous tetrahydrofuran were introduced slowly. The mixture was stirred for 30 minutes at −75° C. and 0.5 g of the product of Step B were introduced. After stirring for 1 hour, 0.375 ml of methyl iodide were added slowly and the mixture was stirred for 90 minutes. The reaction medium then stood so that the temperature rose and the ammonia was eliminated. Then 25 ml of water were added at about 0°/+5° C. The mixture was stirred at +20°/+25° C. for 30 minutes. After extracting with ethyl acetate, the organic phase was washed with water and dried, then the solvent was eliminated. The residue was chromatographed on silica eluting with a cyclohexane-ethyl acetate mixture (91-9) to obtain after crystallization from isopropyl ether, 0.34 g of the expected product melting at 107° C.

IR Spectrum (CHCl$_3$) Absence of acetate-Absorption at 1698 cm$^{-1}$ (non-conjugated ketone). NMR Spectrum (CDCl$_3$, 300 MHz, ppm) 0.60 (s): 18-CH$_3$; 1.04 (t): CH$_3$ of the propyl; 1.12 (s): CH$_3$ in position 17; 3.98: ketal; 5.58: H$_{11}$.

STEP D: cyclic 3-(1,2-ethanediyl) acetal of 17α-methyl-17β-(1,2-dioxo propyl) -5(10), 9(11)estradien-3one 1.5 g of the product of Step C and 15 ml of dimethylformamide were mixed together under an inert gas atmosphere and after stirring at 20° C. for 10 minutes, the reaction medium was cooled to 0°/+5° C. and 1 g of potassium terbutylate was added. The suspension was stirred at 0°/+5° C. for 5 minutes, then cooled to −25° C. and 0.27 liters of oxygen were introduced by bubbling through. The mixture was stirred while allowing the temperature to rise to 0° C. The mixture was poured at 0° C. under inert atmosphere into 30 ml of a 0.2M phosphate buffer and stirred for 30 minutes. After extracting with ethyl acetate, the organic phase was washed with water, dried and the solvent was evaporated. The residue was chromatographed on silica eluting with a toluene-methylene chloride-ethyl acetate mixture (90-7-3) to obtain after crystallization from isopropyl ether, 1.07 g of the expected product melting at approx. 100° C.

IR Spectrum (CHCl$_3$) Absorptions at 1725–1694 cm$^{-1}$(C=O) NMR spectrum (CDCl$_3$, 300 MHz, ppm) 0.66 (s): 18-CH$_3$; 1.26 (s): CH$_3$ in position 17; 2.32 (s): CH$_3$ of the propyl; 3.99: ketal; 5.59: H$_{11}$.

STEP E: 17α-methyl 17β-(1,2-dioxo-propyl)-4,9-estradien-3-one 0.2 g of the product of Step D and 1.5 ml of 99.5% acetic acid were mixed together under an inert gas atmosphere, then 0.075 ml of 65% perchloric acid were added followed by 0.075 ml of water. The mixture was stirred for 2 hours and then a mixture of 5.2 ml of water and 2.8 g of ice was added. Extraction took place with methylene chloride, the organic phase was washed with water, dried and concentrated to dryness. The residue was chromatographed on silica eluting with a toluene-dioxane mixture (95-5) to obtain 0.142 g of the expected product.

IR Spectrum: (CHCl$_3$) Absorptions at 1716–1694 cm$^{-1}$ (C=O), 1653 cm$^{-1}$ (conjugated C=O), 1607 cm$^{-1}$ (C=C). NMR Spectrum: (CDCl$_3$-300 MHz, ppm) 0.86: 18-CH$_3$; 1.26: CH$_3$ in position 17; 2.33: CH$_3$ of the propyl; 5.68: C=C.

STEP F: 17α-methyl-17β-(2S-hydroxy-1-oxo propyl)-4,9-estradien-3-one 500 ml of sodium acetate buffer and 20 g of *Saccharomyces cerevisiae* yeast were mixed together at 30° C. ±1° C. and after stirring for 20 minutes at 30° C., then 6.6 g of glucose were added. While maintaining the temperature at 30° C. and the pH at 5.4 by the addition of 2N sodium hydroxide or 2M acetic acid, 0.1 g of the product of Step E in solution in dimethylsulfoxide was introduced. The mixture was stirred for 22 hours and was then centrifuged for 45 minutes at 20.000 g and at a maximum of 20° C. The supernatant was extracted with ethyl acetate and the aqueous phase was saturated to 50% by the addition of sodium chloride, then extracted again with ethyl acetate. The combined organic phases were washed with water, dried and concentrated to dryness to obtain 100.3 mg of the crude expected product HPLC analysis showed that it contained 99.75% of the 21-OH(S) isomer. 0.090 g of the crude product was chromatographed on silica eluting with a toluene-ethyl acetate —isopropanol mixture (90-6-4) to obtain 0.043 g of the expected product melting at 115° C.

NMR Spectrum (CDCl$_3$-300 MHz, ppm) 0.83 (s): 18-CH$_3$; 1.18 (s): CH$_3$ in position 17; 1.32 (d): CH$_3$—CH—STEP F': 17α-methyl 17β-(2 S-hydroxy 1-oxo propyl)-4,9-estradien-3-one Tests were carried out with the yeasts shown in the table below under the following conditions:

a) The growth of the yeast was carried out on a synthetic type medium (phosphate buffer +source of mineral nitrogen) made up with trace elements and vitamins, the carbon source being glucose. A medium of pH 6.4 was obtained and incubation was carried out at 30° C. on an orbital stirrer at 150 revs/min. for 24 hours.

b) To carry out the bioconversion, 1 volume of growth medium was diluted beforehand in 1 volume of new medium containing a new carbon source constituted by glycerol, at the rate of 40 g/l and a concentration of diketone substrate of 1 g/l. No third solvent was added and a pH of approximately 5.5 was obtained.

The processing of the tests was carried out after variable periods of incubation, under magnetic stirring and the bubbling through of air at approximately 30° C. To do this, 100 μl of the mixture were removed and placed in a tube containing glass balls. 5 ml of chlorobutane were added and the mixture was stirred for 1 minute. The upper phase was collected and the quantity of expected product present was determined by HPLC and related to the total volume of the test. The results are shown in the table below:

| Name of strain | MUCL No.* | Duration of culture hours | Product obtained in mg** |
| --- | --- | --- | --- |
| *Saccharomyces chevalieri* | 27815 | 24 | 62 |
| *Saccharomyces hienipiensis* | 27820 | 24 | 82.5 |
| *Saccharomyces italicus* | 27822 | 24 | 75 |
| *Saccharomyces uvarum* | 27835 | 144 | 60 |
| *Octosporomyces japonicus* | 27840 | 24 | 65 |
| *Octosporomyces octosporus* | 27842 | 24 | 85 |
| *Saccharomyces carlsbergensis* | 28756 | 48 | 30 |
| *Saccharomyces pastorianus* | 29299 | 23 | 57 |
| *Kluyveromyces thermotolerans* | 28822 | 23 | 92.5 |
| *Kluyveromyces marxianus* | 27725 | 23 | 59 |
| *Schizosaccharomyces pombe* | 28824 | 23 | 100.5 |
| *Saccharomyces cerevisiae* | | 23 | 54.5 |

*Yeast strains marketed under this No., from the Mycothèque de l'Université Catholique de Louvain.
**In this case it was the product estimated at the level of the medium, which was purified as described in Stage F.

Various modifications of the process of the invention may be made without departing from the spirit or scope thereof and it should be understood that the invention is intended to be limited only as defined in the appended claims.

What is claimed is:

1. A process for the preparation of a compound of the formula

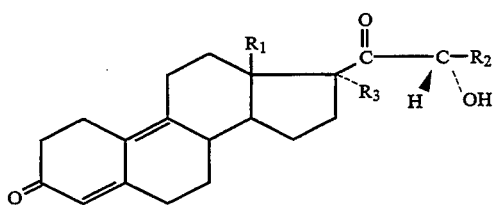

wherein R₁ is alkyl of 1 to 3 carbon atoms, R₂ is alkyl of 1 to 12 carbon atoms and R₃ is alkyl of 1 to 4 carbon atoms comprising reacting a compound of the formula

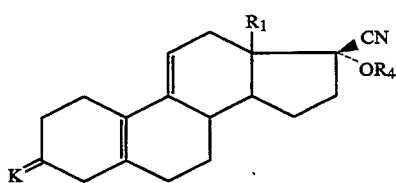

wherein R₄ is a remainder of an easily cleavable ether, K is a protected ketone function in the form of a ketal, thioketal or mixed ketal and R₁ has the above definition with a magnesium organic compound reagent of the formula

HalMg—CH₂—R₂          A wherein Hal is a halogen and R₂ is defined as above to obtain a compound of the formula

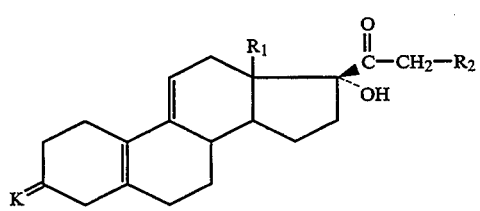

wherein R₁, R₂ and K are defined as above, reacting the latter with an acylation agent to obtain a compound of the formula

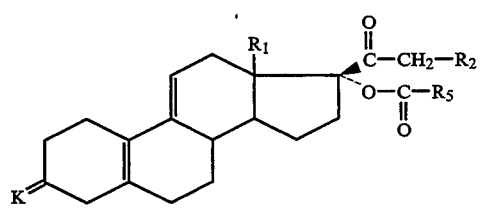

wherein R₅ is alkyl of 1 to 6 carbon atoms or aryl of 6 to 10 carbon atoms and R₁, R₂ and K are defined as above, reacting the latter with an appropriate alkylation agent to obtain a compound of the formula

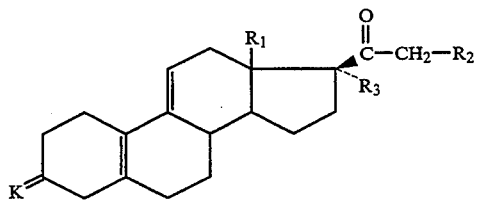

wherein R₁, R₂, R₃ and K are defined as, above, subjecting the latter to autoxidation to obtain a compound of the formula wherein R₁, R₂, R₃ and K are defined as above, reacting the latter with an acid to obtain a reconjugated 3-keto compound of the formula wherein R₁, R₂ and R₃ are defined as above and reacting the latter with a regio- and enantioselective reducing agent to obtain a compound of formula I.

2. The process of claim 1 wherein in the compound of formula II, R₄ is selected from the group consisting of alkyl of 1 to 6 carbon atoms, tetrahydropyranyl, aryl of 6 to 12 carbon atoms and a silylated group.

3. The process of claim 2 wherein R₄ is trialkylsilyl and K is a ketal.

4. The process of claim 1 wherein the acylation agent is acetic anhydride or acetyl chloride or bromide.

5. The process of claim 1 wherein the alkylation agent is an alkyl halide or sulfate.

6. The process of claim 1 wherein the autoxidation reaction is carried out by bubbling oxygen or air through an enolate in position 20 obtained by action of a strong base on the compound of formula V.

7. The process of claim 1 wherein the reduction is carried out enzymatically.

8. The process of claim 7 wherein the reduction is carried out with a yeast.

9. The process of claim 7 wherein the reduction is carried out using a yeast chosen from the class, of Hemiascomycetes.

10. The process of claim 7 wherein the reduction is carried out using *Saccharomyces cerevisiae*.

11. The process of claim 1 wherein R₁ is methyl, R₂ is methyl and the alkylation agent is a methylation agent.

12. A compound of the formula

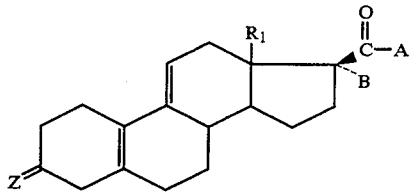

VIII wherein $R_1$ is defined as in claim 1 and (a)Z is K, K being defined as in claim 1, A is $-CH_2-R_2$ and B is $-OH$ or $-O-CO-R_5$, $R_2$ and $R_5$ being defined as in claim 1, or A is $-CO-R_2$ and B is $R_3$, $R_2$ and $R_3$ being defined as in claim 1; or (b)Z is $-O-$, A is $-CO-R_2$ and B is $R_3$, $R_2$ and $R_3$ being defined as in claim 1; or (c)Z is K, A is $-CH_2-R_2$ and B is $R_3$, K, $R_2$ and $R_3$ being defined as in claim 1, with the exception of the compound wherein Z is ethylenedioxy, $R_1$ and B are methyl and A is $-CH_2-CH_3$.

13. A compound of the formula

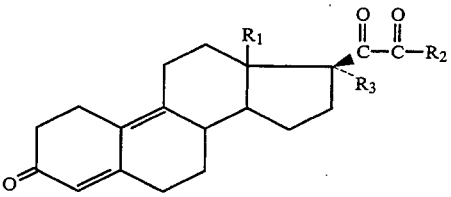

wherein $R_1$, $R_2$, $R_3$ and K are defined as in claim 1.

* * * * *